United States Patent [19]

Pope

[11] Patent Number: 5,007,409

[45] Date of Patent: Apr. 16, 1991

[54] MEDICAL SPECULUM BLADE SHEATH

[76] Inventor: Susan G. Pope, 6025 Bruns Ct., Oakland, Calif. 94611

[21] Appl. No.: 420,759

[22] Filed: Oct. 12, 1989

[51] Int. Cl.⁵ ............................................. A61B 1/32
[52] U.S. Cl. .......................................... 128/17; 128/3
[58] Field of Search ................. 128/17, 18, 6, 10, 11, 128/4; 220/403; 606/147, 148

[56] References Cited

U.S. PATENT DOCUMENTS

| | | | |
|---|---|---|---|
| 3,841,317 | 10/1974 | Awais | 128/17 |
| 3,851,642 | 12/1974 | McDonald | 128/18 |
| 4,492,220 | 1/1985 | Hayes | 128/17 |
| 4,597,382 | 7/1986 | Perez, Jr. | 128/17 |
| 4,813,558 | 3/1989 | Fujiyoshi | 220/903 |

Primary Examiner—Edward M. Coven
Assistant Examiner—Mark S. Graham
Attorney, Agent, or Firm—Linval B. Castle

[57] ABSTRACT

A soft, resilient, silicone rubber sheath for covering each of the cold metal blades of a vaginal speculum reduces the shock of an often painful examination and a possible long-lasting emotional shock to adolescent patients.

3 Claims, 1 Drawing Sheet

MEDICAL SPECULUM BLADE SHEATH

BRIEF SUMMARY OF THE INVENTION

This invention relates to medical speculums and particularly to a disposable blade insulating sheath for reducing pain and the shock of a cold metal speculum blades during clinical examinations.

Gynecology patients often report pain and discomfort resulting from examinations made with cold vaginal speculums, and in cases involving the clinical examination of very young or even preteen rape victims, the combination of pain and cold instruments used in such an examination often produces an emotional shock that leaves a deep psychological impression.

The speculum blade sheath or cover to be described is intended only as a soft, comfortable, disposable insulator for shielding the cold metal blades from the patient. It need not be a bacterial shield as described in U.S. Pat. No. 4,492,220, nor a laser radiation shield as shown in U.S. Pat. No. 4,597,382. While the material of the sheath may also be a bacteria and virus shield, its primary purpose is to reduce the misery and possibility of psychological trauma associated with an often very painful clinical examination.

Briefly described, the blade cover is preferably a silicone rubber sheath molded to substantially conform to both the interior and exterior surfaces of each blade of a speculum. In the preferred embodiment of the blade cover, the sheath thickness is approximately about 0.040 inches in thickness with a solid soft tip about one-quarter inch in length extending past the distal end of each blade. The interior length of the sheath is about three inches, depending upon the speculum blade length, and a finger tab may be added to extend about one inch in from the proximal end to assist in the securing and the removal of each sheath from its blade.

BRIEF DESCRIPTION OF THE DRAWINGS

In the drawings which illustrate the preferred embodiment of the invention.

DETAILED DESCRIPTION

Figure 1:
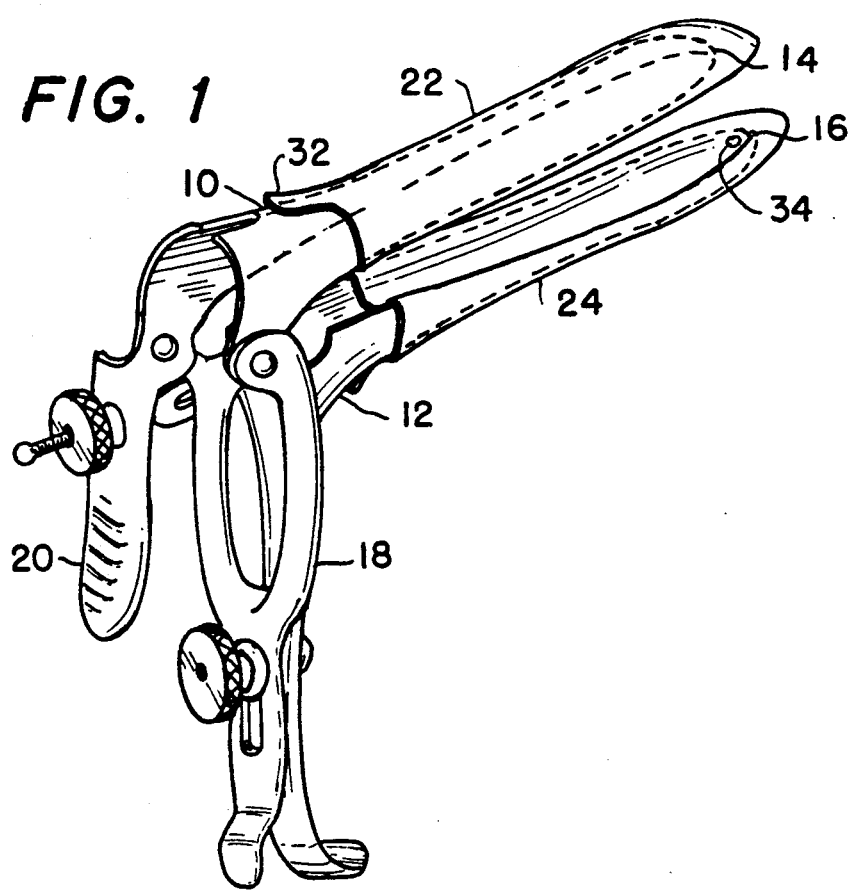
FIG. 1 is a perspective view illustrating a medical speculum with a blade sheath on each blade.
Figure 2:
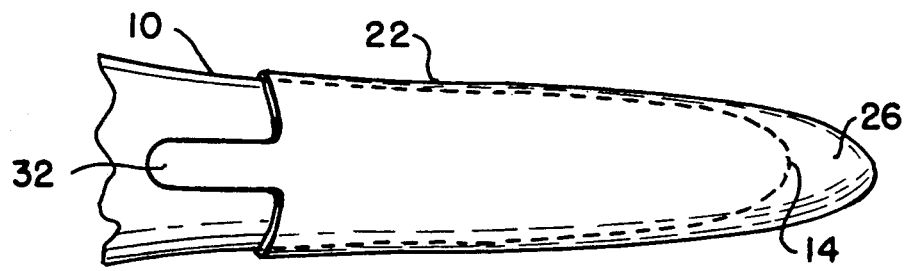
FIG. 2 is a plan view of the exterior of a top or bottom speculum blade and its blade sheath.
Figure 3:
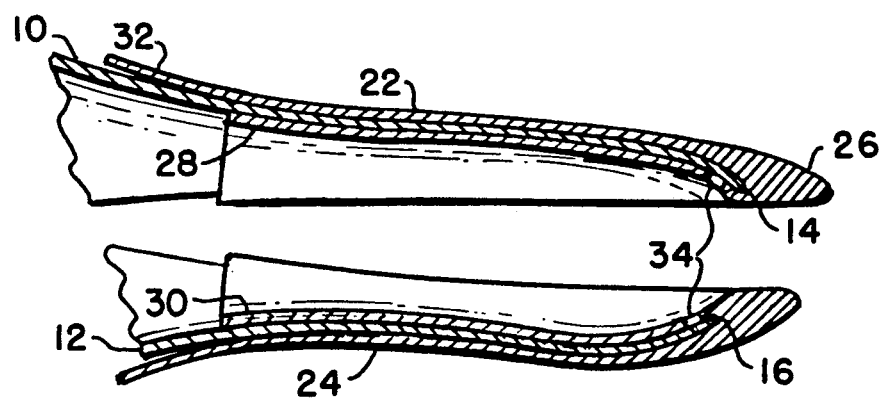
FIG. 3 is a sectional side view of sheathed speculum blades.

The figures illustrate a typical vaginal speculum having a pair of convex, elongated, stainless steel blades 10, 12, each having a substantially semicircular cross section tapering to a blunt distal end 14, 16 and each coupled to a frame member 18 at their proximal end for adjustments of blade spacing and blade opening by a thumb lever 20. As previously discussed, the use of a cold steel speculum in the examination of patients may cause paid and discomfort and, in some very young patients, may result in an emotional shock that may be avoided by the use of warm, soft speculum blades such as obtained by the blade sheathes illustrated in the figures.

The blade sheaths 22, 24 are preferably identical and are soft silicone rubber molded into a semicircular cross section shape to conform to a speculum blade. Each sheath is formed with a longitudinal pocket into which the blade is inserted. The resilient sheath material is approximately 0.040 inches in thickness and the total length of the sheath is about three inches, excluding a tab 32 to be described, but including a solid tapered tip 26 that extends past the blade distal ends 14, 16 by about one-quarter inch. The inner surfaces 28, 30 of the sheaths are concave to roughly conform to the interior surfaces of the steel blades 10, 12. If desired, one or more small air vent holes 34 may be formed in the inner surfaces of the sheaths near the blade distal ends 14, 16 to facilitate the installation and removal of a sheath on a blade.

Extending about one inch along the proximal centerline on the concave surface of each sheath is an optional finger tab 32 about a half inch in width. This tab is preferably a part of the sheath but may be a separate tab secured to the proximal end of the sheath. The tab 32 may be held against the convex surface of a blade by an examining technician to prevent slippage of the sheath on the blade, and later provides a convenient tab for removal of a tightly stretched sheath from a blade.

I claim:

1. A sheath for the blade of a medical speculum having upper and lower elongated metal blades adjustably coupled together at the proximal or rear end, each blade having a substantially semicircular cross section terminating at a distal end, said sheath comprising:

a soft resilient material having a semicircular cross section with a convex first surface and concave second surface separated to form an arcuate longitudinal pocket between an open first end and a closed distal end adapted to receive the speculum blade;

a solid tip on said resilient material, said tip extending past the distal end of said pocket and tapered to a thin soft edge;

a finger tab of material extending lengthwise from said first convex surface of said resilient material at said open first end; and a vent hole between said arcuate pocket and at least one surface of said sheath adjacent the closed distal end thereof to facilitate installation and removal of said sheath from a speculum blade.

2. The sheath claimed in claim 1 wherein said soft resilient material is molded silicone rubber.

3. The sheath claimed in claim 1 wherein said finger tab is formed as a part of the soft resilient material of said sheath.

* * * * *